(12) United States Patent
Wunderink et al.

(10) Patent No.: US 6,383,757 B1
(45) Date of Patent: May 7, 2002

(54) METHODS OF DIAGNOSING COMMUNITY ACQUIRED PNEUMONIA (CAP) AND PREDISPOSITION OR SUSCEPTIBILITY FOR CAP AND ASSOCIATED SEPTIC SHOCK THROUGH DETECTION OF GENE POLYMORPHISMS

(76) Inventors: Richard Glenn Wunderink, 8363 Barncliff Cove, Germantown, TN (US) 38139; Grant William Waterer, 3/13 Hayes Avenue, Yokine 6060, Western Australia (AU)

( * ) Notice: Subject to any disclaimer, the term of this patent is extended or adjusted under 35 U.S.C. 154(b) by 0 days.

(21) Appl. No.: 09/745,129

(22) Filed: Dec. 21, 2000

Related U.S. Application Data

(60) Provisional application No. 60/236,498, filed on Sep. 29, 2000.

(51) Int. Cl.[7] .................................................. C12Q 1/68
(52) U.S. Cl. .............................. 435/6; 435/5; 435/91.1; 435/91.2; 415/195.11; 415/197.11; 415/211.11
(58) Field of Search ............................... 435/5, 6, 91.1, 435/91.2; 415/195.11, 197.11, 211.11

(56) References Cited

PUBLICATIONS

Fine et al., "A Prediction Rule to Identify Low–Risk Patients with Community–Acquired Pneumonia", *New Engl. J. Med.* 1997 336:243–238.

Hirani and MacFarlane, "Impact of management guidelines on the outcome of severe community acquired pneumonia", *Thorax* 1997 52:17–21.

British Thoracic Society, *Q. J. Med.* 1987.

Leeper and Torres, "Community–Acquired Pneumonia in the Intensive Care Unit", *Clin. Chest. Med.* 1995 16:155–171.

Niederman et al., "Guidelines for the Initial management of Adults with Community–acquired Pneumonia:Diagnosis, Assessment of Severity, and Initial Antimocrobial Therapy", *Am. Rev. Resp. Dis.* 1993 148:1418–1426.

Pachon J. et al., "Severe Community–acquired Pneumonia", *Am. Rev. Resp. Dis.* 1990 142:369–373.

Ruiz M. et al., "Severe Community–acquired Phneumonia", *Am. J. Respir. Crit. Care. Med.* 1999 160:923–929.

*Primary Examiner*—W. Gary Jones
*Assistant Examiner*—Janell E. Taylor
(74) *Attorney, Agent, or Firm*—Licata & Tyrrell P.C.

(57) ABSTRACT

A method of diagnosing a disease associated with a genetic polymorphism in a TNFβ gene comprises determining the genotype of said TNFβ gene in an animal. The method can be used to diagnose CAP or diagnose predisposition or susceptibility to CAP. Compositions for said diagnosis are provided. Methods of treatment of CAP or predisposition or susceptibility to CAP are provided, comprising identifying an individual having CAP a predisposition or susceptibility to the disease and subsequently treating that individual in accordance with treatments for such conditions as are known to those of skill in the art. Also provided are methods of identifying and diagnosing a predisposition for septic shock, along with methods of treatment.

7 Claims, No Drawings

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Description of Artificial  Sequence:  Synthetic
```

```
-continued

<400> SEQUENCE: 1
ccgtgcttcg tgctttggac ta                                               22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial  Sequence:  Synthetic

<400> SEQUENCE: 2 agagggtgg atgcttgggt tc                                                22

<210> SEQ ID NO 3
<211> LENGTH: 23
<212> TYPE: DNA
<213> ORGANISM: Artificial Sequence
<220> FEATURE:
<223> OTHER INFORMATION: Description of Artificial  Sequence:  Synthetic

<400> SEQUENCE: 3
aggcaatagg ttttgagggc cat                                              23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial  Sequence:  Synthetic

<400> SEQUENCE: 4
acactcccca tcctccctgc t                                                21
```

METHODS OF DIAGNOSING COMMUNITY ACQUIRED PNEUMONIA (CAP) AND PREDISPOSITION OR SUSCEPTIBILITY FOR CAP AND ASSOCIATED SEPTIC SHOCK THROUGH DETECTION OF GENE POLYMORPHISMS

This application claims the benefit of priority from provisional U.S. Application Ser. No. 60/236,498 filed Sep. 29, 2000.

FIELD OF THE INVENTION

This invention relates to diagnostic methods based upon a polymorphism in the Tumor Necrosis Factor beta gene (TNFPβ; also known as Lymphotoxin alpha), more specifically, an adenine ("A") at the +250 site rather than the usual guanosine ("G"). More specifically, this invention relates to a method for diagnosis of Community Acquired Pneumonia (CAP) and diagnosing pre-disposition or susceptibility to CAP, by screening for the presence of this polymorphism, either alone or in combination with a polymorphism at the 308 locus. The invention also relates to compositions for screening for the polymorphism and improved treatment choices for patients diagnosed with CAP or as being susceptible to CAP by the method of the present invention. Further, this invention relates to identifying and diagnosing pre-disposition for septic shock in patients with CAP.

BACKGROUND OF THE INVENTION

Pneumonia is a common clinical entity, particularly among the elderly. CAP is a major health problem worldwide. In the United States, CAP is the leading cause of death due to infection and the sixth most common cause of death overall. Clinically, CAP exhibits an enormous variety in the severity of presentation, from fulminant septic shock at one end of the spectrum to almost asymptomatic disease at the other. A thorough understanding of the epidemiology and microbiology of Community Acquired Pneumonia (CAP) is essential for appropriate diagnosis and management. Although the microbiology of CAP has remained relatively stable over the last decade, there is new information on the incidence of atypical pathogens, particularly in patients not admitted to hospital, and new information on the incidence of pathogens in cases of CAP and in CAP in the elderly. Recent studies have provided new data on risk-factors for mortality in CAP, which can assist the clinician in making decisions about the need for hospital admission. The emergence of antimicrobial resistance in *Streptococcus pneumonia*, the organism responsible for most cases of CAP, has greatly affected the approach to therapy, especially in those patients who are treated empirically. Guidelines for the therapy of CAP have been published by the American Thoracic Society, the British Thoracic Society, and, most recently, the Infectious Diseases Society of America and others. These guidelines differ in their emphasis on empirical versus pathogenic-specific management.

CAP remains a significant health problem and patients continue to die despite receiving appropriate antibiotic therapy. Modification of the host immune response, both anti- and pro-inflammatory approaches, has yet to live up to the promise of improved outcome. Despite this, there is significant reason for optimism. Some immunomodulatory therapies clearly have efficacy in some patients. As the understanding of the immune response to pneumonia improves, the ability to tailor specific therapies for individual patients will also improve, hopefully avoiding the deleterious effects that have so far prevented the development of an effective immune-based therapy. The possibility of delivering cytokines directly to the lung, is a particularly promising way of achieving the desired pulmonary effect without systemic side effects. Corticosteroids are currently unique in that they have a proven role in the therapy of pneumonia due to *P. carinii*. The development of pathogen specific therapies, such as INF for *L. pneumophila*, based on an improved understanding of host-pathogen interactions, are awaited.

Once respiratory failure has ensued, supportive measures such as patient positioning and differential lung ventilation can improve oxygenation at no additional risk in some patients, particularly those with severe unilateral pneumonia. In facilities where ECMO is available it may be beneficial in selected patients when all other means of providing respiratory support have failed. The role of inhaled NO and partial liquid ventilation is also currently unclear and awaiting further study.

The past 20 years has seen an explosion in knowledge of human immunology and exploration of the therapeutic possibilities is just beginning. The next 10 years promises to finally provide a significant advance in the therapy of pneumonia, the first substantial gain since penicillin.

In light of the prevalence of CAP and the evolution of resistance in the most common bacterial CAP pathogen, physicians advise obtaining specimens for culture of CAP pathogens and analysis of patterns of susceptibility, especially of *S. pneumonia*, in their communities; using antibiotics appropriately and prudently, according to prevailing susceptibilities when empirical treatment is called for; and immunizing susceptible patients with pneumococcal and influenza vaccines. This is because the mortality of patients with CAP approaches or may exceed 20%, compared to less than 1% for patients with non-severe CAP (Fine et al. *New Engl. J. Med.* 1997;336:243–250, British Thoracic Society, *Q. J. Med* 1987;239:192–220, Niederman et al. *Am. Rev. Resp. Dis.* 1993;148:1418–1426). In such cases an ability to improve accuracy of diagnosis of, or predisposition or susceptibility to CAP, would be of distinct advantage and may lead to improved outcomes and lower medical costs for such patients.

TNF acts on many healthy cells in addition to cancer cells. It is important in regulating immune and inflammatory response and plays a large role in septic shock. It is released by a variety of cells including red and white blood cells, cells that line blood vessels, nervous system cells, muscle cells, bone cells, and some tumor cells. Although it was first observed to kill certain tumor cells (sarcoma cells), TNF has been found to help some tumors grow. In addition, TNF can be very toxic to normal cells. Early experiments found that administering TNF caused fever and loss of appetite. TNF also has been shown to affect the metabolism of many cell types, causing them to need more oxygen. It has been found to play a role in many autoimmune diseases, such as rheumatoid arthritis and myasthenia gravis. Certain viral and bacterial infections can cause healthy cells to produce elevated levels of TNF.

It is a surprising feature of the present invention to be able to diagnose the presence of CAP and the predisposition or susceptibility to CAP by the method of the present invention.

BRIEF SUMMARY OF THE INVENTION

It is an object of the present invention to improve diagnosis of CAP. It is a particular object of the invention to provide a method of diagnosis of predisposition or susceptibility to CAP. A further object is to provide, following such diagnosis, a method of identifying patients for alternative management of CAP before the disease becomes significantly established. Thus, the invention also relates to compositions for screening for the TNFβ polymorphism at the +250 site and improved treatment choices for patients diagnosed with CAP or as being susceptible to CAP by the method of the present invention. A further object of the present invention is to identify and diagnose CAP patients at an increased risk for CAP associated septic shock.

Other preferred embodiments of the present invention will be apparent to one of ordinary skill in light of the following description of the invention and of the claims.

DETAILED DESCRIPTION OF THE INVENTION

In a first aspect, the invention provides a method of diagnosing a disease associated with a genetic polymorphism (adenine ("A") at the +250 site rather than the usual guanosine ("G")) in a TNFβ gene in an animal predisposed or susceptible to said disease, said method comprising determining the genotype of TNFβ in said animal. The first aspect of the invention further provides a method of identifying an animal predisposed or susceptible to a disease associated with a genetic polymorphism in a TNFβ gene, said method comprising determining the genotype of said TNFβ gene in said animal. In an embodiment of the invention, the method of diagnosis is to screen for an individual at risk of a condition or disease such as CAP correlated with a TNFβ gene polymorphism ("A") at the +250 site.

The invention is based upon a correlation between polymorphisms in the TNFβ gene, specifically at position +250, and predisposition or susceptibility to CAP. The invention is of advantage in that by screening for the presence of the polymorphism it is possible to identify individuals likely to have a genetic predisposition or susceptibility to the disease. It may also result in substantially different management, both prevention and treatment, if pneumonia occurs, with subsequent substantial improvement in mortality and morbidity from CAP.

In an embodiment of the invention, diagnosis is carried out by determining whether a TNFβ gene contains a polymorphism "A" at position +250. Possessing a fragment that contains the "A" at that +250 site correlates with increased risk of predisposition or susceptibility to CAP. As a human genome contains two TNFβ genes, one on each of a pair of chromosomes, an individual can accordingly be found to be homozygous or heterozygous for the risk polymorphism, or to lack the risk polymorphism.

Genotypic and allelic frequencies of this invention are readily determined by a number of methods known to those skilled in the art. Methods used in the present invention are shown in Example 1 below and include using PCR amplification and restriction enzyme digestion. The method conveniently comprises amplifying a fragment of a TNFβ gene to produce copies and determining whether copies of the fragment contain the polymorphism.

Another suitable technique is to amplify the fragment using PCR techniques, producing copies of a fragment that is at least 500 base pairs in length, preferably at least 600 base pairs in length. It is preferred that the PCR primers are selected so as to amplify a region of the gene that is about 740 base pairs in length. PCR techniques are well known in the art and it would be within the ambit of a person of ordinary skill in this art to identify primers for amplifying a suitable section of the applicable exon of the TNFβ gene. PCR techniques are described for example in EP-A-0200362 and EP-A-0201 184. In a further embodiment of the invention, the diagnostic method comprises analysis of the TNFβ gene using single strand conformational polymorphism (SSCP) mapping to determine whether the TNFβ gene is the risk or the non-risk form.

In preferred embodiments, the method comprises screening a TNFβ gene, and this screening is conveniently carried out by any one of a number of suitable techniques that are known in the art, and may be conveniently selected from amplification of a nucleic acid sequence located within the TNFβ gene, Southern blotting of regions of the gene and single strand conformational polymorphism mapping of regions within the gene or as described in Example 1 below. The genotype in that region is also optionally determined using hybridization probes adapted selectively to hybridize with the particular polymorphism of the TNFβ gene at the +250 location which is associated with predisposition or susceptibility to disease. A probe used for hybridization detection methods must be in some way labeled so as to enable detection of successfully hybridization events. This is optionally achieved by in vitro methods such as nick-translation, replacing nucleotides in the probe by radioactively labeled nucleotides, or by random primer extension, in which non-labeled molecules act as a template for the synthesis of labeled copies. Other standard method of labeling probes so as to detect hybridization are known to those skilled in this art.

According to a second aspect of the invention, there is provided a method of diagnosis and therapy comprising diagnosing CAP and diagnosing predisposition or susceptibility to CAP according to the method of the invention and treating an individual having such CAP or a predisposition or susceptibility to CAP thereby treating to prevent or lessen CAP.

Known therapies for CAP can be effective in halting advancement of the disease, or at least slowing the advancement. TNFβ+250 gene analysis may also lead to more appropriate placement of patients into intensive care/critical care units, an important factor in optimizing survival from CAP. It is thus an advantage of the invention that early diagnosis of CAP is improved, so that preventative therapy can be started as soon as possible, optimizing any interventions potential (such as immunomodulatory therapy) for affecting outcome. As alternative diagnostic methods improve and are developed, so the invention can add to the total knowledge of the risk of developing CAP of an individual. The decision of a physician on how and whether to initiate therapy in anticipation of the disease can be taken with increased confidence.

A variety of suitable treatments of CAP are described in the art. See e.g., Hirani and MacFarlane *Thorax* 1997;52:17–21, Pachon J et al. *Am. Rev. Resp. Dis.* 1990;142:369–373, Ruiz M et al. *Am. J. Respir. Crit. Care. Med.* 1999;160:923–929, Leeper and Torres *Clin. Chest. Med.* 1995;16:155–171. Other treatments are known to persons of skill in the art.

Another aspect of the invention provides a composition for use in diagnosing a disease associated with a genetic polymorphism in a TNFβ gene in an animal predisposed or susceptible to said disease, said composition comprising one or more primer nucleic acid molecules adapted to amplify a portion of a TNFβ gene selected from a portion of the gene around the +250 location.

Another aspect of the invention also provides a composition for use in identifying an animal predisposed or susceptible to a disease associated with a genetic polymorphism in a TNFβ gene, said compositions comprising one or more primer nucleic acid molecules adapted to amplify a portion of the TNFβ gene selected from a portion of the gene around the +250 location.

The composition of this aspect of the invention may comprise a nucleic acid molecule capable of identifying the +250 polymorphism in said TNFβ gene, said polymorphism being indicative of a risk genotype in said animal.

A further embodiment of the invention provides a composition for diagnosis of CAP or predisposition or susceptibility to CAP, comprising means for determining genotype of a TNFβ gene of an individual, for example whether an individual is homozygous or heterozygous for polymorphic variants of a TNFβ gene at the +250 location such as the method provided in the Example 1 herein.

In an embodiment of the invention, a diagnostic composition comprises PCR primers adapted to amplify a DNA sequence within and around the TNF +250 polymorph location, wherein alternative versions of the gene are distinguished one from another.

In a further aspect of the invention there is provided a diagnostic kit comprising a diagnostic composition as described above and an indicator composition for indicating how possessing a polymorphic version of a TNFβ gene correlates with the presence of CAP or redisposition or susceptibility to CAP.

Diagnostic kits are typically accompanied by or comprise a chart or other visual aid for assistance in interpreting the results obtained using the kit. Suitable indicator compositions for use in the diagnostic kit of the invention include a leaflet or other visual reminder that possessing the risk polymorphism version of a TNFβ gene correlates with CAP or the increased risk of predisposition or susceptibility to CAP.

In a still further aspect of the invention there is provided use, in the manufacture of means for diagnosing whether an individual has a predisposition or susceptibility to CAP, of PCR primers adapted to amplify a region around +250 in the TNFβ gene. Alternative versions of the gene are typically distinguished one from another by means known to those skilled in the art.

Multiple techniques exist and are known to one skilled in the art in the manufacture of means for diagnosing whether an individual has CAP or a predisposition or susceptibility to CAP, of PCR primers adapted to amplify a region around 250 in the TNFβ gene. Restriction analysis can be employed, where the enzyme cuts if a "G" is present, but not if an "A" is present, and when run on a, e.g., 1% agarose gel, the different fragments migrate differently based upon size.

According to the invention, an individual who is homozygous for a risk polymorphism, that is to say homozygous for a version of 250 ("AA"), is classified as being at highest risk of CAP or predisposition or susceptibility to CAP. An individual being heterozygous ("GA") is classified as having moderate risk of CAP or predisposition or susceptibility to CAP.

Optionally, the assessment of an individual's risk factor according to any aspect of the invention is calculated by determining the genotype of a TNFβ gene polymorphism and combining the result with analysis of other known genetic, physiological, dietary, clinical, or other indications known to those of skill in the art. The invention in this way provides further information on which measurement of an individual's risk can be based.

It is possible that CAP polymorphisms are not the disease causing genes. Nevertheless, the observed correlation is of use in diagnosis of CAP and of risk of predisposition or susceptibility to CAP.

In another embodiment of the invention, the results of the genotyping done herein are used, along with other diagnostics measures and disease parameters, by treatment providers to determine the best course of treatment for the patient having CAP or having been determined as susceptible to CAP by the methods of this invention.

In another aspect of the invention, a method of identification and diagnosis of patients with CAP at an increased risk of septic shock is provided. A significant association between the LTα+250 genotype and the risk of septic shock in patients with CAP has been identified. In addition, analysis of LTα+250: TNFα−308 haplotypes strongly suggests that the LTα+250 locus is not the causative polymorphism. This finding sheds some light on the relative importance of the LTα+250 and TNFα−308 loci with respect to CAP.

Haplotype analysis has shown that the lowest risk of septic shock is in patients with two 250G:308G haplotypes. It is believed that the TNFα−308 locus does exert an influence, but is largely masked by the much greater prevalence of the A allele at the LTα+250 locus in the population. This shows the important role that differences in local allelic frequencies play in evaluating the significance of gene.

These findings have important implications for understanding the inflammatory response to severe infections. In an effort to identify patients at high risk for subsequent septic shock, the systemic inflammatory response syndrome (SIRS) criteria were developed. SIRS is defined as having at least two of the following four conditions: (1) oral temperature of >38° C. or <36° C.; (2) respiratory rate of >20 breaths/minute or $Pa_{co2}$ or <32 count torr; (3) heart rate of >90 beats/minute; (4) leukocyte count of >12,000/μl or <4,000/μl or >10% bands. Hypoxemia was included as an organ dysfunction and is one of the two most common organ dysfunctions in most studies of SIRS. Hypoxemia (and other organ dysfunctions in SIRS) is assumed to occur by the same mechanism and reflect the same pro-inflammatory state as septic shock. This unexpected finding that respiratory failure is not associated with a TNF hypersecretor genotype, with a trend to greater respiratory failure with a TNF hyposecretor genotype (LTα+250 GG) is not consistent with this understanding of SIRS.

It is believed that LTα+250 is not directly causative, but is a marker for the 'real' polymorphism which is located within the 250A:308G haplotype. The A:G haplotype is considered a risk version of the gene. This has important implications not only for understanding the molecular basis for susceptibility to septic shock, but also for other studies showing association between disease states and LTα+250 genotype. It is further believed that both polymorphisms may be causative, but an A allele at one locus interferes with the mechanism leading to increased TNFα production, (such as a conformation change that affects the binding of transcription activating factors) with the A allele at the other locus.

Clearly non-genetic factors such as the length of time to initial therapy and adequacy of therapy also play important roles in the ultimate development of the clinical presentation, including the development of septic shock. These studies did not control for the length of time from onset of symptoms to presentation. However, this data supports the hypothesis that genetic polymorphisms play a critical role in the variable presentation of CAP.

Differences in the virulence of pathogens also has an impact on outcome of CAP. These experiments did not analyze the influence of genotype on CAP for individual pathogens due to the low number of cases with a definite microbiological diagnosis. The problem of the low sensitivity of traditional culture techniques in CAP is well known, and the diagnostic rate observed is not inconsistent with studies of the yield of cultures in patients with CAP. However, the pattern in patients with proven or suspected pneumococcal CAP parallels that of the entire cohort, a finding which is not surprising given that the pneumococcus is the most common cause of CAP.

Septic shock is associated with the TNFα high secretor genotype (AA) at the LTα+250 locus while type I respiratory failure in the absence of septic shock is associated with the low secretor (GG) genotype. The TNFα–308 polymorphism appears to have the similar associations, but a lesser influence in this cohort due to the comparative rarity of the TNFα–308A allele and linkage disequilibrium with the LTα+250 polymorphism. The finding that these two presentations of CAP have opposite associations with respect to TNFα secretion raises significant concern regarding the validity of the SIRS definition as an inclusion criteria for anti-inflammatory sepsis trials.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following example, which is included herewith for purposes of illustration only and is not intended to be limiting of the invention.

EXAMPLE 1

A number of TNFβ gene polymorphisms that influence TNFβ production have been identified. The TNFbetab +250 A/A genotype has been associated with increased TNFβ production and increased mortality in patients with septic shock. It has surprisingly now been found that the A/A genotype influences the presentation of patients with community acquired pneumonia (CAP).

Subjects were recruited as part of a prospective cohort study of patients with CAP. Patients in this study were diagnosed as having CAP and required inotropic or ventilatory support. Genotypic and allelic frequencies were determined using PCR amplification and restriction enzyme digestion. Results are expressed as number (%). The significance of trends was assessed using Chi-Squared analysis.

The results showed that 108 patients were successfully genotyped. Table 1 shows the genotype distribution in the subgroups of interest. There was a trend to an increased proportion of CAP based on genotype, AA (0.24)>GA(0.11) >GG(0.06) (p=0.06).

TABLE 1

|  | A/A | G/A | G/G | Total |
|---|---|---|---|---|
| Non CAP | 22(24) | 54(58) | 17(18 | 93 |
| CAP | 7(47) | 7(47) | 1(7) | 15 |
| Total | 29(27) | 61(57) | 18(17) | 108 |

EXAMPLE 2
Septic Shock Association with TNFα

Patients in this study were diagnosed with CAP and exhibited symptoms for less than 14 days. The presence of a new chest radiographic infiltrate was confirmed by either a Radiologist or a Pulmonary/Critical Care physician, and clinical features were suggestive of acute pneumonia. The clinical features required were one of group A (fever (>37.8° C.), hypothermia (<36.0° C. ), cough, sputum production); or two of group B (dyspnea, pleuritic pain, physical findings of lung consolidation, and leukocyte count of >12×10$^9$/l or <4.5×10$^9$/L)

No patients with severe immunodeficiency as defined by the Center for Disease Control criteria for patients with the Acquired Immune Deficiency syndrome; no patients receiving chemotherapy in the past 60 days; no patients receiving treatment with corticosteroids equivalent to prednisolone >2mg per day for more than 14 days; no patients receiving immunosuppression following organ transplantation; no patients on cyclosporine, cyclophosphamide or azathioprine; no patients from nursing homes who were non-ambulatory; and no patients hospitalized within the past 30 days were included in the study.

All patients were assessed by a pulmonary physician (GWW or RGW) within 24 hours of presentation. The majority of patients were seen in the Emergency Department at the time of admission. Pneumonia Severity Index (PSI) scores using the clinical data available at the time of presentation were calculated as described by Fine and colleagues. Acute physiologic and chronic health evaluation (APACHE) II scores were calculated using the worst physiological values during the first 24 hours after presentation. Results of microbiological and other laboratory tests as ordered by the treating physician were recorded.

Septic shock was defined using ACCP-SCCM criteria. To meet the criteria for septic shock, a documented systolic blood pressure of <90 mmHg for at least 30 minutes in the absence of any other causes of shock, and at least 4 hours of inotropic support after adequate fluid replacement were required.

Respiratory failure was defined as an oxygen saturation of <90% on room air. If the corresponding arterial $PCO_2$ was <45mmHg, the patient was classified as having Type I respiratory failure. A corresponding arterial pCO2 ≧45 mmHg defined Type II respiratory failure.

Septic shock or respiratory failure had to occur within 48 hours of presentation to hospital for the patient to be classified as having one of these two end points. Patients were classified in a blinded fashion, i.e. without any knowledge of genotype information.

Whole blood for genotypic analysis was collected, transferred into 1.5 ml cryotubes and stored at −70° F. until processed. DNA was extracted from the whole blood samples using the Genomic DNA Purification Kit (Promega, Madison, Wis.). The genotypic analysis was also performed in a blinded fashion, that is, the analysis was performed without knowledge of any clinical data including end points such as mortality, septic shock and respiratory failure.

The LTα+250 polymorphism contains an NcoI restriction site when the G allele is present. A 782 basepair (bp) fragment was amplified in a PCR mixture containing 20 ng of DNA, 20 pmol each of the primers TNFβ+250-1 (5'-CCGTGCTTCGTGCTTTGGACTA-3'; SEQ ID NO: 1) and TNFβ+250-2 (5'-AGAGGGGTGGATGCTTGGGTTC-3'; SEQ ID NO: 2), 1 unit of Taq polymerase, 1× reaction buffer (Promega), 500 μM each of deoxy-adenosing triphosphate, deoxy-cytidine triphosphate, deoxy-guanosine triphosphate, deoxy-thymidine triphosphate, and 2.5 nM of $MgCl_2$. Reaction conditions were as follows: 35 cycles of denaturation at 94°C. for 30 seconds, annealing at 69° C. for 30 seconds, and extension at 74° C. for 42 seconds. The amplified DNA was incubated with NcoI and the fragments were analyzed by electrophoresis in a 1% agarose gel and visualized by ethidium bromide staining. Interpretation was as follows: a single band of 782 bp identified individuals homozygous for an adenine at the LTα+250 locus; two bands at 586 and 196 bp identified individuals homozygous for a guanine at the LTα+250 locus; three bands at 782, 586, and 196 bp identified individuals heterozygous at the LTα+250 locus.

The region containing the TNFα–308 locus was amplified using the primers TNFα–308–1 (5'-AGGCAATAGGTTTTGAGGGCCAT-3'; SEQ ID NO: 3) and TNFα–308–2 (5'-ACACTCCCCATCCTCCCTGCT-3'; SEQ ID NO: 4). The TNFα–308–1 primer contains 4 bp of the NcoI recognition sequence including a mismatched cytosine as shown by the C in the TNFα–308–1 primer sequence. This mismatched cytosine allows for creation of an NcoI restriction site (CCATGG) when the G allele is present at position –308. A 116 bp PCR product was generated using the following reaction conditions: 35 cycles of denaturation at 95° C. for 30 seconds, annealing at 64° C. for 15 seconds, and extension at 74° C. for 15 seconds. The amplified DNA was incubated with NcoI and the treated fragments were analyzed by electrophoresis in an 8% polyacrylamide gel and visualized by ethidium bromide staining. Interpretation was as follows: a single band at 116 bp identified individuals homozygous for a adenine at the TNFα–308 locus; two bands at 96 and 20 bp identified individuals homozygous for a guanine at the TNFα–308 locus; three bands at 116, 96, and 20 bp identified individual heterozygous at the TNFα–308 locus.

All statistical calculations, including multivariate analysis, were performed using the statistical package JMP version 3.2.2 (SAS Institute Inc., Cary, N.C.). Unless otherwise stated, results are expressed as mean+/–standard deviation. Relative risks (RR) are reported as RR (95% confidence intervals). The statistical significance of differences in continuous variables were calculated using Student's t-test (after confirming they were normally distributed), and for categorical variables with Fisher's exact test. The significance of trends was assessed using Chi-squared analysis, except for the haplotype analysis where the Kruskal-Wallis test of association with one ordered category was used. All reported p values are two-tailed with a value of <0.05 considered significant. Results: A total of 300 subjects consented to participate in the study. Twenty subjects were subsequently determined to have a diagnosis other than CAP and excluded from analysis. In 17 of the 20 subjects excluded, subsequent review of old chest radiographs the infiltrate seen on admission was determined to be chronic. The 3 other subjects excluded were also subsequently determined to have a diagnosis other than pneumonia (malignancy—2, pulmonary embolus—1).

The mean age of the 280 study patients was 57.9 years (range 18–98). There were 146 (52.1%) female subjects and 134 (47.9%) male subjects, with 158 (56.4%) African American, 121 (43.2%) and one (0.3%) Asian subject. The distribution of subjects by PSI grade was I—36 (12.9%), II—78 (27.9%), III—59 (21.1%), IV—72 (25.7%) and V—35 (12.5%).

A pathogen was identified from blood cultures in 30 patients (10.7%) and from sputum cultures in an additional 12 patients (4.2%), giving an etiological diagnosis in 42 patients (15.0%). The most common pathogens isolated were *Streptococcus pneumoniae, Pseudomonas aeruginosa, Streptococcus viridans,* and *Haemophilus influenzae.* Four patients had more than one pathogen identified. An additional 50 patients (17.9%) had negative blood and sputum cultures but the sputum gram stain was consistent with infection due to *S.pneumoniae.*

As has been noted previously, a significant linkage disequilibrium was found between the two polymorphisms (p<0.001). A homozygotes at the TNFβ+250 locus were G homozygotes at the TNFα–308 locus, the A allele at TNFα+250 was not always associated with the G allele at TNFα–308.

There were 25 deaths (8.9 %). Table 2 shows a comparison of age, mortality, APACHE II scores and PSI scores by genotype at each locus. There were no significant differences between genotypes at either locus. The trend to decreasing APACHE II scores between LTα+250 AA and LTα+250 GG genotypes did not reach statistical significance (p=0.12).

TABLE 2

Comparison of Mortality, Mean Age, APACHEII scores and Pneumonia Severity Index

|  | LTα + 250 AA | LTα + 250 GA | LTα + 250 GG | TNFα-308AA | TNFα-308 GAA | TNFα-308 GC |
|---|---|---|---|---|---|---|
| Number | 84 | 137 | 59 | 19 | 64 | 197 |
| Age (years) mean (SD) | 59.3 (17.9) | 58.8 (19.4) | 53.8 (19.5) | 62.8 (16.0) | 58.9 (19.6) | 57.1 (18.8) |
| Mortality | 10 (11.9%) | 10 (7.3%) | 5 (8.5%) | 2 (10.5%) | 6 (9.3%) | 17 (8.6%) |
| APACHE II mean (SD) | 14.2 (9.1) | 12.4 (7.2) | 11.8 (7.9) | 12.2 (7.0) | 12.6 (7.2) | 12.9 (8.3) |
| PSI points mean (SD) | 87.6 (41.6) | 84.5 (40.3) | 75.8 (40.3) | 85.1 (36.3) | 79.5 (34.6) | 84.8 (43.0) |

All 31 subjects who met the criteria for septic shock required inotropic support for greater than 24 hours, except 2 subjects who died within the first 24 hours after admission. AA homozygotes were significantly more likely to develop septic shock than non-AA homozygotes (p=0.01), with a relative risk of 2.48 (1.28–4.78). This attributable risk of the LTα+250 AA genotype to the development of septic shock in the population was therefore 30.7%.

The proportion of subjects developing septic shock within each TNFα–308 genotype was AA-0.16, GA-0.06 and GG-0.12 (p–NS). Carriage of an AA genotype at either the LTα+250 locus or the TNFα-308 locus was associated with a significantly increased risk of septic shock (18.0% vs 6.8%, p=0.006, RR 2.51 (1.30–4.87)).

In nominal logistic regression analysis incorporating age, sex, a history of cardiac or renal disease, alcohol consumption, LTα+250 and TNFα–308 genotype, the only factors that remained significant predictors of septic shock were LTα+250 genotype (p=0.03) and increasing age (p=0.048). The age adjusted odds ratio for septic shock in carriers of the LTα+250 AA genotype was 3.64 (1.28–10.66).

The data was then reanalyzed by LTα+250:TNFα–308 haplotype carriage to determine whether this made the association between the LTα+250 A allele and septic shock more specific. Since haplotypes cannot be unequivocally assigned to heterozygotes at both loci, they are scored as a 0.5 probability for each haplotype. Carriage of the 250A:308G haplotype was associated with a significantly greater risk of septic shock (p=0.014 by Kruskal-Wallis test of association with one ordered category, Table 3).

TABLE 3

The risk of septic shock and LTα + 250A:TNFα-308G haplotype carriage

| Number of LTα + 250A:TNFα-308G haplotypes | 2 | 1 | 0.5 | 0 |
|---|---|---|---|---|
| Septic Shock | 16 | 7 | 3 | 5 |
| No Septic Shock | 68 | 71 | 48 | 52 | p=0.014 Kruskal-Wallis test of association with one ordered category

No association between the risk of septic shock and carriage of the 250A:308A or 250G:308A haplotypes (Tables 4 and 5) was found. However, the trend to a decreased risk of septic shock with the 250G:308G haplotype was significant (p=0.011, Table 6).

TABLE 4

The risk of septic shock and LTα + 250A:TNFα-308A haplotype carriage

| Number of LTα + 250A:TNFα -308A haplotypes | 2 | 1 | 0.5 | 0 |
|---|---|---|---|---|
| Septic shock | 0 | 0 | 3 | 28 |
| No Septic Shock | 0 | 8 | 48 | 193 | p=0.0966 Kruskal-Wallis test of association with one ordered category

TABLE 5

The risk of septic shock and LTα + 250G:TNFα-308A haplotype carriage

| Number of LTα +250G:TNFα-308A haplotypes | 2 | 1 | 0.5 | 0 |
|---|---|---|---|---|
| Septic Shock | 3 | 1 | 3 | 24 |
| No Septic Shock | 8 | 20 | 48 | 173 | p=0.5033 Kruskal-Wallis test of association with one ordered category

TABLE 6

The risk of septic shock and LTα + 250G:TNFα-308G haplotype carriage

| Number of LTα + 250G:TNFα-308G haplotypes | 2 | 1 | 0.5 | 0 |
|---|---|---|---|---|
| Septic Shock | 1 | 8 | 3 | 19 |
| No Septic Shack | 34 | 83 | 48 | 94 | p=0.0111 by Kruskal-Wallis test of association with one ordered category

Fifteen patients with septic shock died (48.4%). The mortality rate from septic shock within each genotype was LTα+250: AA-50.0%, GA-50.0%, GG-40.0%; TNFα–308 AA-66.6%, GA-25.0%, GG-50.0%. There were no statistically significant differences between mortality rates for individual genotypes with either polymorphism or by LTα+250:TNFα–308 haplotype.

There were insufficient subjects with a definitive microbiological diagnosis to analyze the polymorphism data by specific pathogens. However, pooling all patients with proven or suspected pneumococcal disease (n=74), the same trends were seen as were observed in the CAP cohort as a whole.

One hundred and three subjects (36.8%) met the criteria for respiratory failure, 80 with type I and 23 with type II. With respect to the arbitrary cutoff between type I and type II, all subjects classified as type II respiratory failure had at least one pCO2>48 mmHg.

The proportion of subjects developing type 1 respiratory failure within each genotype was LTα+250: AA-0.28, GA-0.25, GG-0.37; TNFα–308 AA-0.32, GA-0.30, GG-0.28. For type II respiratory failure it was LTα+250: AA-0.07, GA-0.11, GG-0.03; TNFα–308 AA-0.11, GA-0.14, GG-0.06. There were no significant differences between genotypes at either locus for type I or type II respiratory failure.

No statistically significant associations between the risk of Type I respiratory failure and any LTα+250: TNFα–308 haplotype was demonstrated.

What is claimed is:

1. A method of diagnosing Community Acquired Pneumonia (CAP) associated with a genetic polymorphism in a TNFβ gene at the +250 locus in an animal, said method comprising determining the genotype at the +250 locus of the TNFβ gene in an animal, and diagnosing CAP based on said genotype.

2. A method of identifying an animal predisposed or susceptible to CAP associated with a genetic polymorphism in a TNFβ gene at the +250 locus, said method comprising determining the genotype at the +250 locus of the TNFβ gene in an animal, and identifying said animal based on said genotype.

3. The method of claim 1 or claim 2 comprising determining whether an individual is homozygous or heterozygous for alternative versions of a TNFβ gene at the +250 locus.

4. A method of diagnosis of CAP or diagnosis of predisposition or susceptibility to CAP in an individual, the method comprising determining whether the individual possesses a polymorphic risk version of a TNFβ gene at the +250 locus, a polymorphic risk version of the gene being one that has an A at site 250, the method comprising:

(a) using restriction analysis with an enzyme capable of cutting the TNFβ gene if a "G" is present at the +250 site and not "A"
   (b) testing whether the copies contain an A or a G at site 250 through known differences in how such fragments migrate on a gel, and thereby determining whether the individual is homozygous or heterozygous for a polymorphic risk version of the gene, and (c) diagnosing the presence of CAP in an individual or diagnose an individual's predisposition or susceptibility to CAP as greatest if that individual is homozygous for the polymorphic risk version of the gene at the +250 site (AA), moderate if that individual is heterozygous for the polymorphic risk version at the +250 site (GA), and least if that individual lacks the polymorphic risk version at the +250 site (GG).

5. A method of managing and treating patients with a predisposition to or who are susceptible to CAP or having CAP comprising, determining whether the individual possesses a polymorphic risk version of a TNFβ gene at the +250 locus, a polymorphic risk version of the gene being one that has an "A" at site 250, wherein the management and treatment of such patient having such polymorphism are promptly treated and managed as if such patient has CAP or is predisposed or susceptible to CAP.

6. The method of claim 4 further comprising determining whether the individual possesses a polymorphic risk version of a TNFα-gene at the 308 locus, and assessing the individual's predisposition to CAP related septic shock.

7. A method of diagnosing patients with CAP at an increased risk of septic shock comprising determining whether the patient possesses a polymorphic risk version gene wherein a polymorphic risk version gene is a TNFβ gene with an adenine at the +250 site or a TNFα gene with an adenine at the −308 site.

* * * * *

UNITED STATES PATENT AND TRADEMARK OFFICE
CERTIFICATE OF CORRECTION

PATENT NO. : 6,383,757 B1
DATED : May 7, 2002
INVENTOR(S) : Wunderink et al.

It is certified that error appears in the above-identified patent and that said Letters Patent is hereby corrected as shown below:

Column 8,
Line 13, please delete "2 mg" and insert -- 20 mg --.
Line 37, please delete "$PC0_2$" and insert -- $_pC02$ --.

Signed and Sealed this

Eleventh Day of November, 2003

JAMES E. ROGAN
*Director of the United States Patent and Trademark Office*